(12) United States Patent
Hsiao

(10) Patent No.: US 9,206,963 B2
(45) Date of Patent: *Dec. 8, 2015

(54) AROMA DIFFUSING NIGHT LAMP ASSEMBLY

(71) Applicant: Ming Jen Hsiao, Mialo County (TW)

(72) Inventor: Ming Jen Hsiao, Mialo County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/796,689

(22) Filed: Jul. 10, 2015

(65) Prior Publication Data

US 2015/0314028 A1  Nov. 5, 2015

Related U.S. Application Data

(63) Continuation-in-part of application No. 13/669,354, filed on Nov. 5, 2012, now Pat. No. 9,109,780.

(51) Int. Cl.
| | |
|---|---|
| F21V 33/00 | (2006.01) |
| F21V 15/00 | (2015.01) |
| F21S 8/00 | (2006.01) |
| A61L 9/00 | (2006.01) |
| A61L 9/12 | (2006.01) |
| A61L 2/00 | (2006.01) |

(52) U.S. Cl.
CPC . *F21V 15/00* (2013.01); *A61L 2/00* (2013.01); *A61L 9/00* (2013.01); *A61L 9/127* (2013.01); *F21S 8/035* (2013.01); *A61L 2209/12* (2013.01)

(58) Field of Classification Search
CPC ............ F21S 8/035; F21V 15/00; A61L 2/00; A61L 9/00; A61L 9/127
USPC .......................................................... 362/96
See application file for complete search history.

(56) References Cited

U.S. PATENT DOCUMENTS

| | | | |
|---|---|---|---|
| 6,085,026 A | 7/2000 | Hammons et al. | |
| 6,921,180 B2 | 7/2005 | Huang | |
| 8,066,420 B2 | 11/2011 | Hsiao | |
| 8,147,097 B1 | 4/2012 | Hsiao | |
| 2009/0310330 A1 | 12/2009 | Vann et al. | |

*Primary Examiner* — Jason Moon Han
(74) *Attorney, Agent, or Firm* — Ming Chow; Sinorica, LLC

(57) ABSTRACT

An aroma-diffusing night lamp assembly includes a body holding a coupling socket at the top, a lamp bulb inserted into the coupling socket and electrically connected to the body, a lampshade defining a bottom coupling hole coupled to the coupling socket and a top opening for holding an aroma capsule, and an aroma capsule including a disposable heat-transfer container mounted in the top opening of the lampshade and an aromatic substance contained in the disposable heat-transfer container and heatable by the radiating heat energy of the lamp bulb to release an aromatic smell.

17 Claims, 6 Drawing Sheets

AROMA DIFFUSING NIGHT LAMP ASSEMBLY

CROSS-REFERENCE TO RELATED APPLICATION

The present application is a continuation-in-part of U.S. application Ser. No. 13/669,354, filed on 5 Nov. 2012, now pending.

BACKGROUND OF THE INVENTION

1. Field of the Invention

This invention relates night lamp technology and more particularly, to an aroma diffusing night lamp assembly, which ensures a high level of safety.

2. Description of the Related Art

The patent of U.S. Pat. No. 8,147,097B1 discloses a night lamps with an added aroma diffusing function. However, the user needs to prepare a particular container for holding an aromatic wax or essential oil, and then to carefully pick up the aromatic wax or essential oil from the container and to put the aromatic wax or essential oil in an accommodation chamber at a top side of a ceramic container above the lampshade for heating by the radiating heat energy of the lamp bulb. During application, the lamp bulb may be contaminated by the aromatic wax or essential oil. Further, when the aromatic wax or essential oil is used up, the user needs to clean the accommodation chamber, avoiding mixing of different aromatic substances or smells. Further, if the accommodation chamber is made of a fragile material, such as ceramic or glass, the accommodation chamber may be broken easily during cleaning.

Further, U.S. Pat. No. 6,921,180B2 discloses a connector of a C-type bulb assembly, which includes two half symmetric pieces, wherein the first piece having its two side projections provided with related rods and the second piece having its two side projections provided with related apertures. The two half pieces can be assembled together to become the connector while the bulb holder is connected therein, and the holder with the connector is capable of being assembled or disassembled with the shell easily and quickly. Because this design can easily be assembled or disassembled and because the lamp bulb is exposed to the outside when electrically conducted, a child may damage the lamp bulb when playing the connector of a C-type bulb assembly for fun, causing an electric shock accident.

SUMMARY OF THE INVENTION

The present invention has been accomplished under the circumstances in view. It is therefore the main object of the present invention to provide an aroma-diffusing night lamp assembly, which prevents a careless user or child from directly touching the lamp bulb, and enables a user to replace the lamp bulb safely.

To achieve this and other objects of the present invention, an aroma-diffusing night lamp assembly comprises body electrically connectable to a power supply outlet for power input and comprising a coupling socket located at a top side thereof, a lamp bulb inserted into the coupling socket and electrically connected to the body, a lampshade connected to the coupling socket to surround the lamp bulb and comprising a top opening located at a top side thereof and a bottom coupling hole located at a bottom wall thereof and coupled to the coupling socket, and an aroma capsule, which comprises a disposable heat-transfer container mounted in the top opening of the lampshade and defining a top opening and adapted for receiving radiating heat energy from the lamp bulb, an aromatic substance contained in the disposable heat-transfer container and heatable by the radiating heat energy to release an aromatic smell, a breathing film sealed to the top opening of the disposable heat-transfer container, and a sealing film bonded to the disposable heat-transfer container over the breathing film to seal the aromatic substance in the disposable heat-transfer container.

Preferably, the body is made in the form of an electrical plug and pivotally coupled with the coupling socket in such a manner that the electrical plug is rotatable relative to the coupling socket and selectively positioned in one of a series of angular positions such as 90°, 180°, 270° and 360° to fit different installation requirements.

Further, the lampshade comprises at least one slot cut through the bottom wall thereof and radially extended from the bottom coupling hole. Further, the coupling socket comprises at least one retaining rod radially extended from an outer perimeter thereof at a top side and insertable through the at least one insertion slot of the lampshade and stoppable at a top side of the bottom wall of the lampshade upon a rotary motion of the lampshade relative to the coupling socket and a locating flange coupling socket extending around the outer perimeter of the coupling socket at a bottom side and stoppable at a bottom side of the bottom wall of the lampshade. The body further comprises a screw holder protruded from the periphery thereof, and a screw mounted at the screw holder and rotatable into one insertion slot of the lampshade to lock the lampshade to the coupling socket.

DETAILED DESCRIPTION OF THE PREFERRED EMBODIMENT

Figure 1:
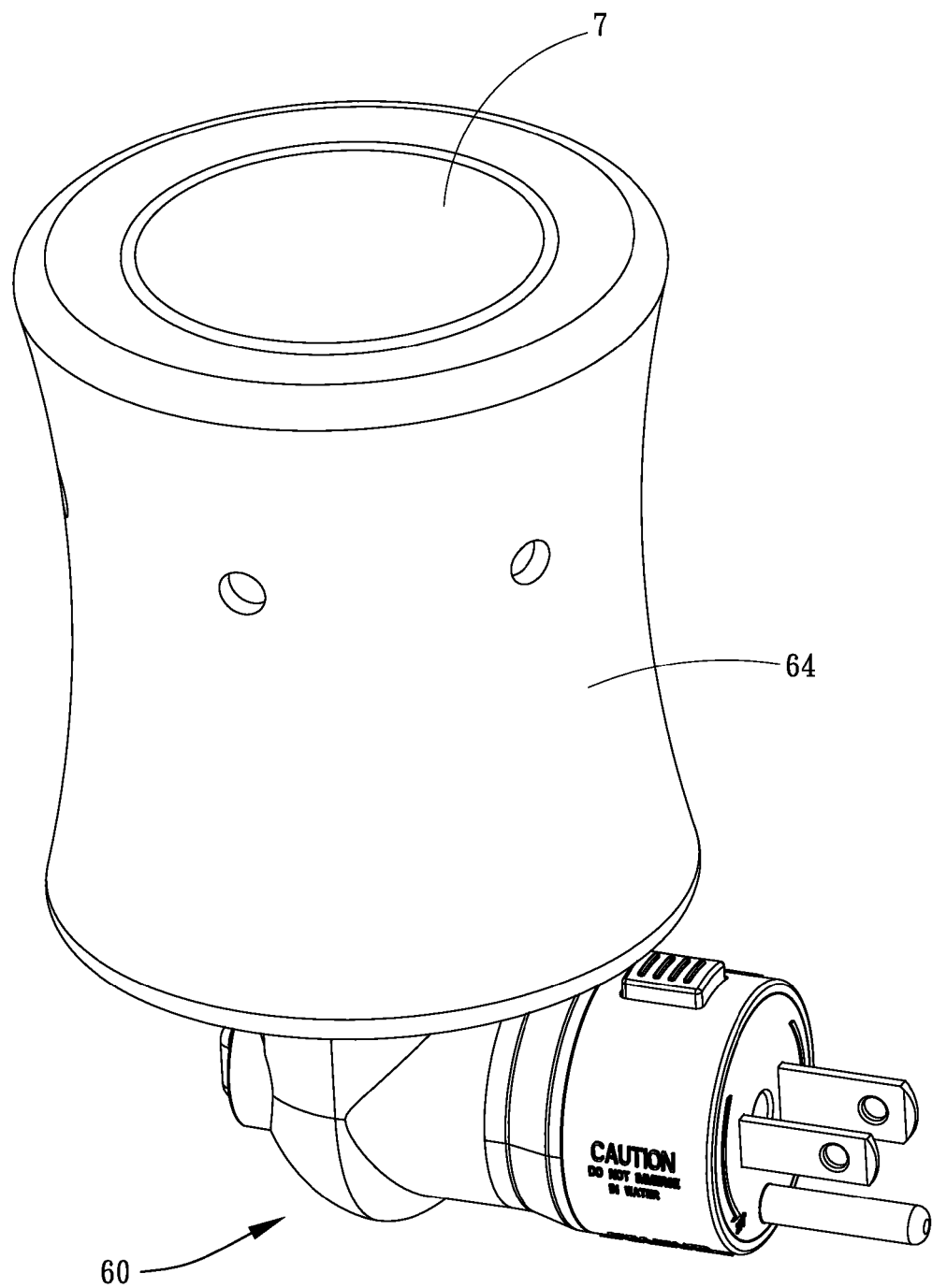
FIG. 1 is an elevational view of an aroma-diffusing night lamp assembly in accordance with a first embodiment of the present invention.
Figure 2:
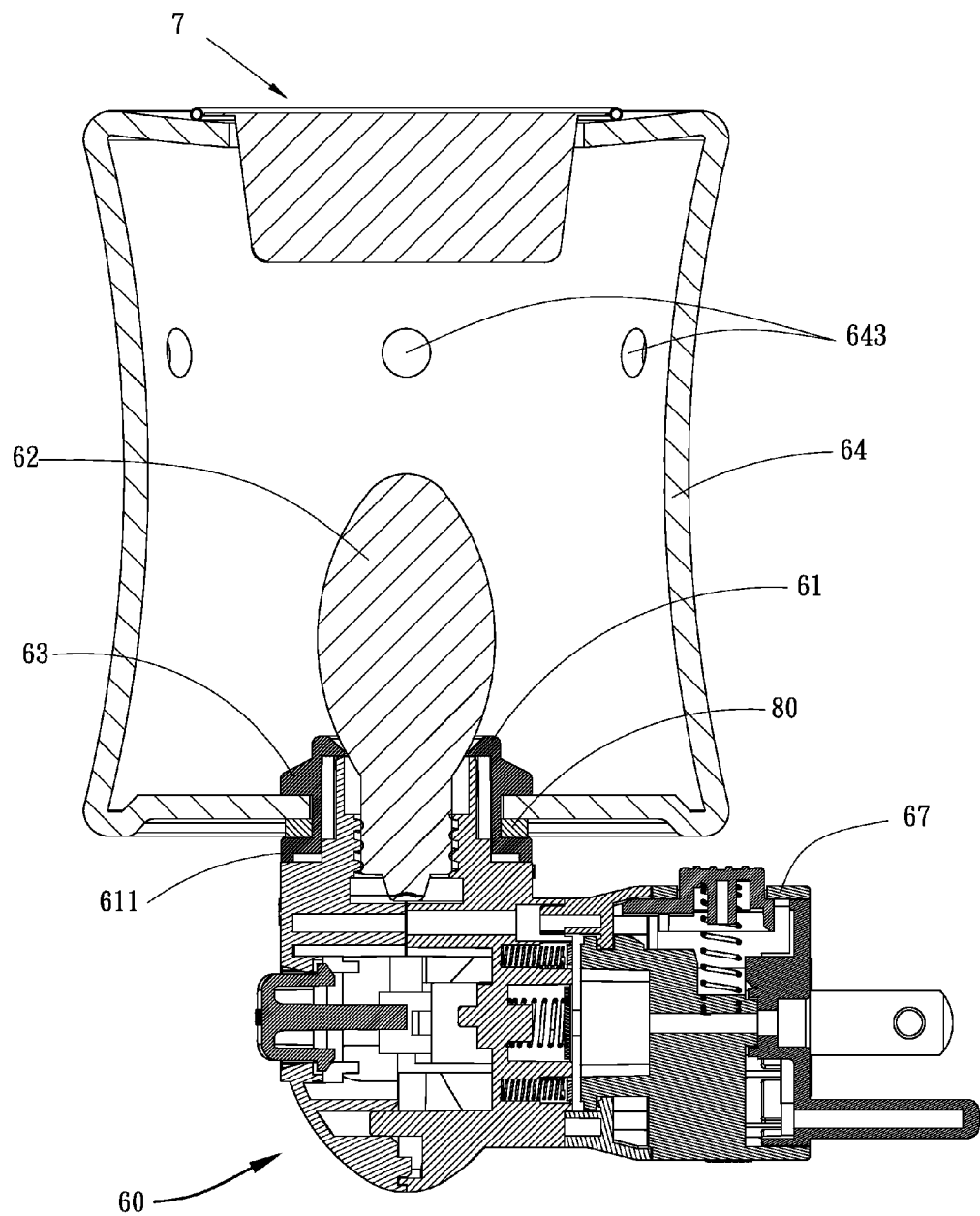
FIG. 2 is a sectional view of the aroma-diffusing night lamp assembly in accordance with the first embodiment of the present invention.
Figure 3:
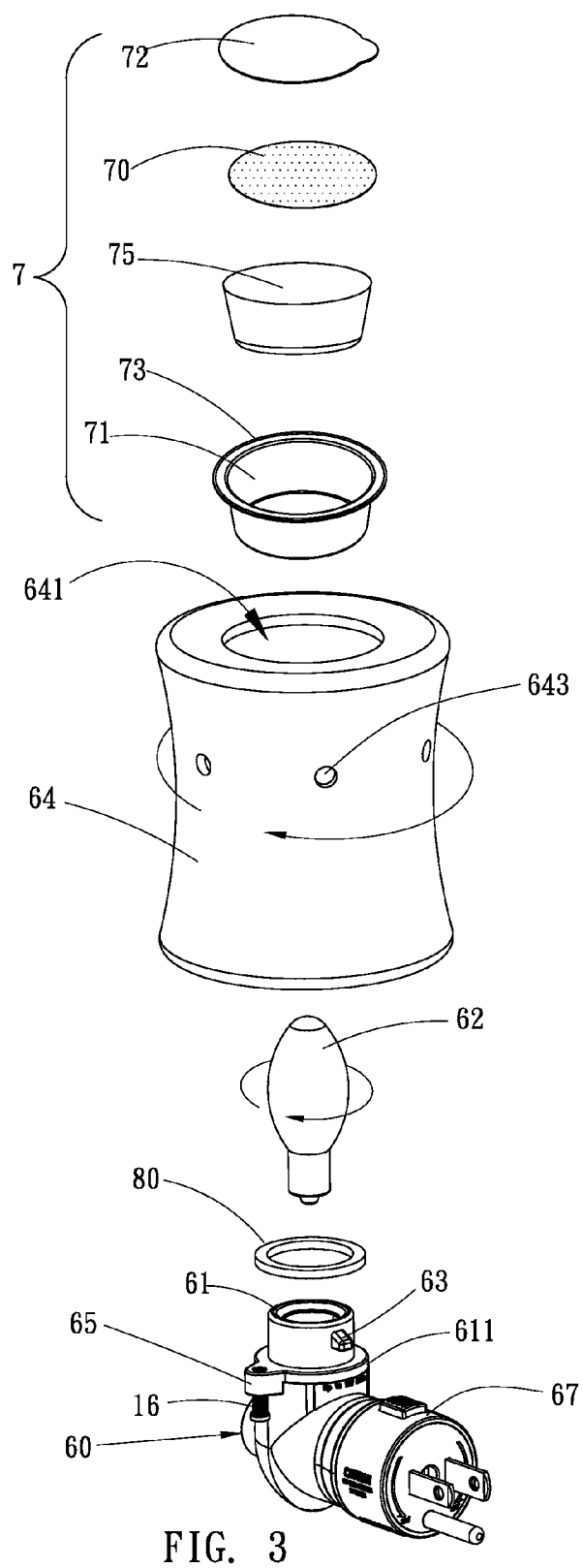
FIG. 3 is another exploded view of the aroma-diffusing night lamp assembly in accordance with the present invention.

Referring to FIGS. 1-3, an aroma-diffusing night lamp assembly in accordance with the present invention is shown comprising a body 60, which is configured to connect to an electric outlet and holds a coupling socket 61 at the top side thereof, a lamp bulb 62 of, for example, 110V or 120V, 15 W installed in the coupling socket 61 and electrically connected to the body 60, a lampshade 64 adapted to surround the lamp bulb 62 and having a bottom coupling hole 643 located at a bottom side thereof and coupled to the coupling socket 61 and a top opening 641 located at an opposing side thereof, and an aroma capsule 7, which comprises a disposable heat-transfer container 71 mounted in the top opening 641 and defining a top opening 73, an aromatic substance 75, preferably, the aromatic substance 75 is a solid aromatic substance put in the disposable heat-transfer container 71, a breathing film 70 sealed to the top opening 73 of the disposable heat-transfer container 71, and a sealing film 72 bonded to the disposable heat-transfer container 71 over the breathing film 70 to seal the aromatic substance 75 in the disposable heat-transfer container 71 and to maintain the quality of the aromatic substance 75. Further, an user can take off the sealing film 72 before using said aroma capsule at once.

Preferably, the body 60 is made in the form of an electrical plug and pivotally coupled with the aforesaid coupling socket 61 such that the electrical plug 67 can be rotated relative to the coupling socket 61 and selectively positioned in one of a series of angular positions, for example, 90°, 180°, 270° and 360° to fit different installation requirements.

Further, the lamp bulb 62 can be a tungsten filament-based incandescent bulb, non-filament lamp bulb or LED light bulb.

Further, the lampshade 64 can be prepared from the material group of ceramics, metal, plastics, fabrics and composite materials.

Further, the lampshade 64 can be transparent, semi-transparent, translucent or semi-translucent.

Preferably, the lampshade 64 is configured to provide air vents 643 for dissipating heat, wherein said lampshade 64 is configured to provide air vents 643 for dissipating heat or radiating light of the lamp bulb 62, the air vents 643 can be configured according to a predetermined decorative design.

Further, embodiment of the present invention the aromatic substance 75 can be a solid aromatic substance, for example said aromatic substance is an aromatic wax.

Further, embodiment of the present invention the aromatic substance 75 can be an aromatic substance, an aromatic wax or a perfume block or an essential oil gel.

Further, commercial aroma diffusers are commonly capable of diffusing an aromatic smell when heated to the temperature of 35~75° C. The lamp bulb 62 can heat the aroma capsule 7 to the temperature of 35~75° C., causing the aroma capsule 7 to diffuse a good smell into the outside open air. Under this temperature range, the disposable heat-transfer container 71 will not melt or deform and can efficiently transfer heat energy produced by the lamp bulb 62 to the aromatic substance 75. The disposable heat-transfer container 71 can be a thin metal film container, a hard plastic container, or a fiber bowl made of a plant fiber such as corn fiber, glass fiber or carbon fiber.

Preferably, the disposable heat-transfer container 71 is made of aluminum film, having the characteristics of lightweight, thin wall thickness and good heat conductivity. Thus, the disposable heat-transfer container 71 can transfer heat energy produced by the lamp bulb 62 to the aromatic substance 75 rapidly, causing the aromatic substance 75 to diffuse a good smell. Further, the disposable heat-transfer container 71 is tough and not easily breakable, eliminating the fragile drawback of ceramic or glass containers that are commonly used in conventional aroma diffusers for holding an essential oil. Further, the sealing film 72 seals the aromatic substance 75 in the disposable heat-transfer container 71, maintaining the quality of the aromatic substance 75. Further, the aromatic substance 75 is sealed in the disposable heat-transfer container 71. When using the aromatic substance 75, the user simply needs to remove the sealing film 72 from the disposable heat-transfer container 71 without contacting the aromatic substance 75. Further, after the aromatic substance 75 is used up, the user can remove the disposable heat-transfer container 71 from the top opening 641 of the lampshade 64, and then put a new aroma capsule 7 in the top opening 641 of the lampshade 64 to replace the used aroma capsule without the necessity of cleaning the used aroma capsule. Further, because the disposable heat-transfer container 71 is made of aluminum foil, it is not breakable. Thus, the user needs not to worry about breaking down the disposable heat-transfer container 71. Further, the user needs not to prepare an extra container for holding the aromatic substance 75.

Further, the breathing film 70 is selected from the material group of nonwoven fabric, fiber cloth, woven fabric, porous plastic membrane and porous silicon rubber, and adapted to guide diffusing aromatic smell upwardly through open spaces therein toward the outside open air. An user can remove the sealing film 72 from the disposable heat-transfer container 71 conveniently, and then put the disposable heat-transfer container 71 in the top opening 641 of the lampshade 64 and then heated by the lamp bulb 62, causing the aromatic substance 75 to release a pleasant smell. If the aroma-diffusing night lamp assembly falls to the floor accidentally, the breathing film 70 still can keep the molten aromatic substance in the disposable heat-transfer container 71, preventing the molten aromatic substance from flowing into the coupling socket 61, the body 60 and the lampshade 64 to contaminate the lamp bulb 62 or to wet the internal circuit of the body 60, ensuring a high level of safety.

Figure 4:
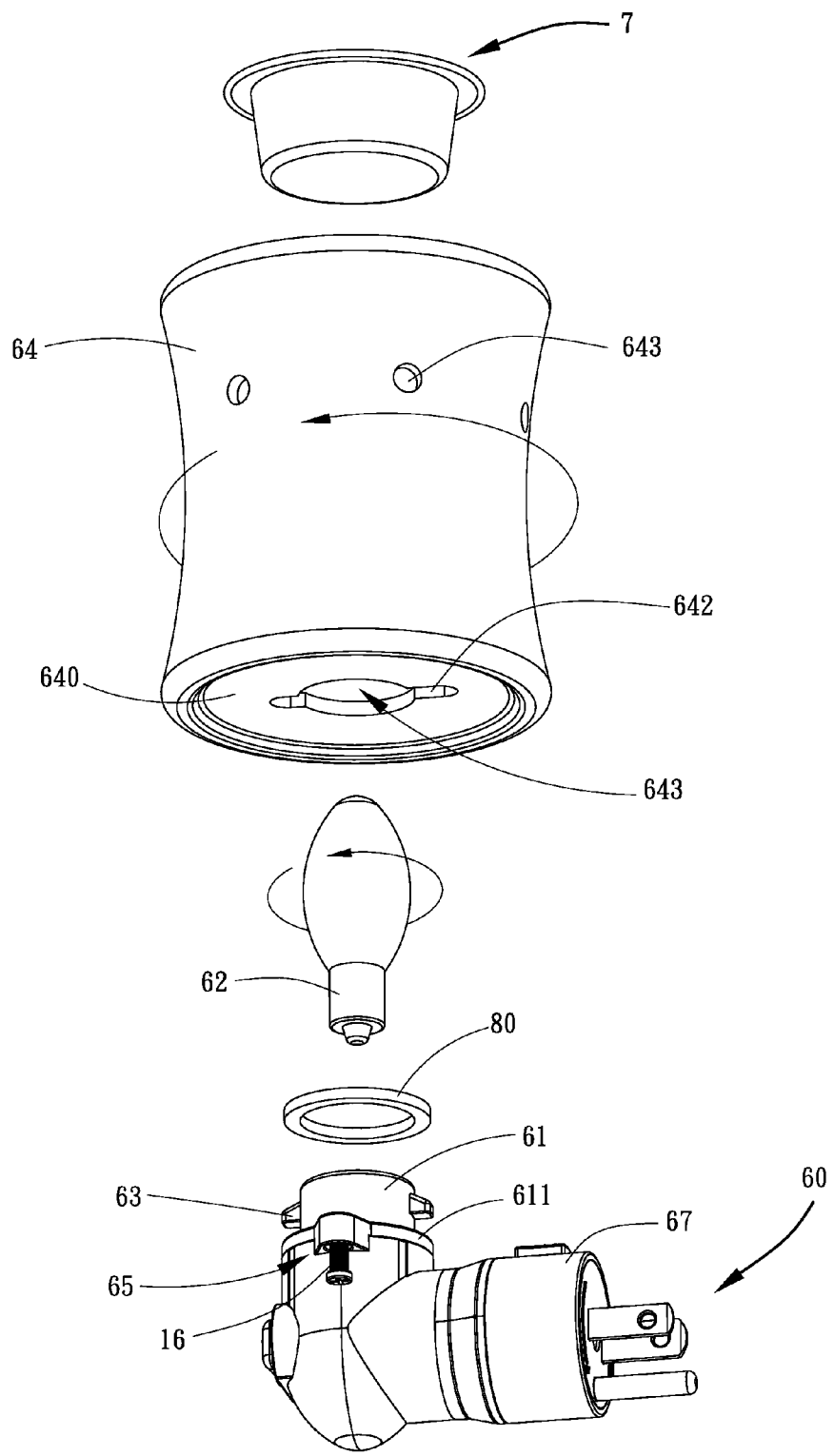
FIG. 4 is still another exploded view of the aroma-diffusing night lamp assembly in accordance with the present invention.
Figure 5:
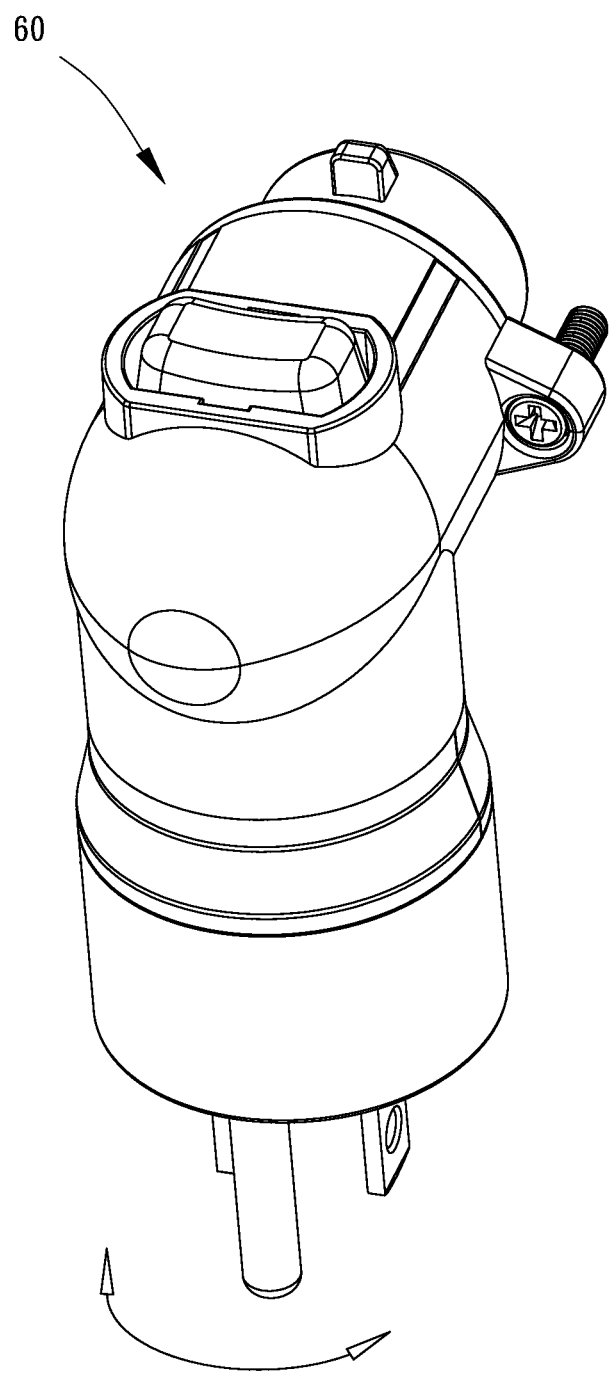
FIG. 5 is an elevational view of the body of the aroma-diffusing night lamp assembly in accordance with the present invention.
Figure 6:
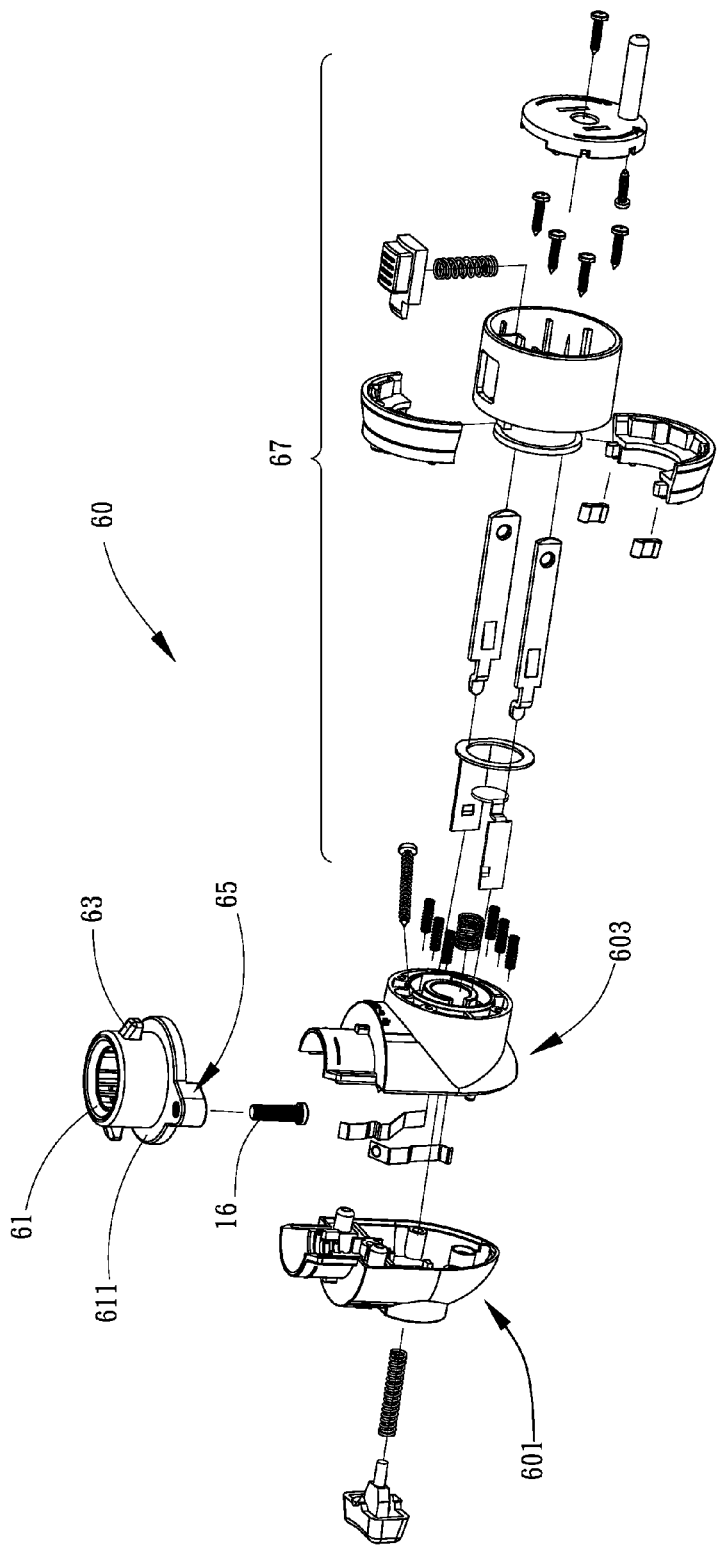
FIG. 6 is an exploded view of the body of the aroma-diffusing night lamp assembly in accordance with the present invention.

Referring to FIGS. 4-6, the coupling socket 61 that is provided at the top side of the body 60 comprises two retaining rods 63 symmetrically protruded from the outer perimeter thereof near the top, and a locating flange 611 extending around the outer perimeter at the bottom side. Further, the body 60 comprises a screw holder 65 extended from the periphery thereof.

Referring to FIG. 4 again, the bottom coupling hole 643 of the lampshade 64 is located on the bottom wall 640 of the lampshade 64. The lampshade 64 further comprises two insertion slots 642 cut through the bottom wall 640 and radially extended from the bottom coupling hole 643 at two sides. When coupling the lampshade 64 to the coupling socket 61, aim the two retaining rods 63 of the coupling socket 61 at the two insertion slots 642 of the lampshade 64, and then insert the coupling socket 61 into the bottom coupling hole 643 of the lampshade 64, and then rotate the lampshade 64 relative to the coupling socket 61 through an angle to let the bottom wall 640 of the lampshade 64 be retained between the two retaining rods 63 and locating flange 611 of the coupling socket 61, and then drive a screw 16 through the screw holder 65 into one insertion slot 642 of the lampshade 64, thereby locking the lampshade 64 to the coupling socket 61.

Referring to FIG. 5, when going to replace the lamp bulb, use a tool, for example, screw driver, to rotate the screw 16 in the reversed direction, moving the screw 16 away from the from the respective insertion slot 642 of the lampshade 64. At this time, the user can rotate the lampshade 74 relative to the coupling socket 61 to the position where the two insertion slots 642 of the lampshade 64 are respectively kept in alignment with the two retaining rods 63 of the coupling socket 61, and then remove the lampshade 64 from the coupling socket 61 for allowing change of the lamp bulb 62. According to the present invention, a careless user or child cannot directly touch or detach the lamp bulb 62. The invention provides a measure for enabling the user to replace the lamp bulb 62 safely, not only complying with electrical safety regulations, but also eliminating the drawbacks of conventional aroma diffusing night lamps.

Referring to FIGS. 4 and 6, the number of the insertion slots 642 of the lampshade 64 and the number of the retaining rods 63 of the coupling socket 61 are preferably 2, ensuring positioning stability between the lampshade 64 and the coupling socket 61 (body 60). However, this number design is not a limitation.

Further, the two insertion slots 642 of the lampshade 64 can be made having different lengths so that the screw 16 can be inserted into the insertion slot 642 that is relatively longer.

Referring to FIG. 6, the body 60 comprises an electrically insulative socket housing consisting of a first socket housing cover shell 601 and a second socket housing cover shell 603 that are fixedly fastened together by the aforesaid coupling socket 61. The aforesaid screw holder 65 is formed with the periphery of the locating flange 611 of the coupling socket 61 for the mounting of the screw 16 that can be inserted into one insertion slot 642 of the lampshade 64 to lock the lampshade 64 and the coupling socket 61 together.

Referring to FIG. 4, a rubber cushion ring 70 is set between the locating flange 611 of the coupling socket 61 and the bottom all 640 of the lampshade 64 to enhance connection stability between the lampshade 64 and the coupling socket 61.

Although a particular embodiment of the invention has been described in detail for purposes of illustration, various modifications and enhancements may be made without departing from the spirit and scope of the invention. Accordingly, the invention is not to be limited except as by the appended claims. the invention is not to be limited except as by the appended claims.

What the invention claimed is:

1. An aroma-diffusing night lamp assembly, comprising:
a body electrically connectable to a power supply outlet for power input, said body comprising a coupling socket located at a top side thereof;
a lamp bulb inserted into said coupling socket and electrically connected to said body;
a lampshade connected to said coupling socket to surround said lamp bulb, said lampshade comprising a top opening located at a top side thereof, and a bottom coupling hole located at a bottom wall thereof and coupled to said coupling socket; and
an aroma capsule comprising an aromatic substance positioned in the top opening of said lampshade and heatable by said radiating heat energy from said lamp bulb to release an aromatic smell;
wherein said body is made in the form of an electrical plug and pivotally coupled with said coupling socket in such a manner that said electrical plug is rotatable relative to said coupling socket and selectively positioned in one of a series of angular positions to fit different installation requirements, and
wherein said lampshade comprises at least one slot cut through the bottom wall thereof and radially extended from said bottom coupling hole; said coupling socket comprises at least one retaining rod radially extended from an outer perimeter thereof at a top side and insertable through said at least one insertion slot of said lampshade and stoppable at a top side of the bottom wall of said lampshade upon a rotary motion of said lampshade relative to said coupling socket and a locating flange extending around the outer perimeter of said coupling socket at a bottom side and stoppable; said body further comprises a screw holder protruded from the periphery thereof and a screw mounted at said screw holder and rotatable into one said insertion slot of said lampshade to lock said lampshade to said coupling socket.

2. The aroma-diffusing night lamp assembly as claimed in claim 1, wherein said aroma capsule further comprises a disposable heat-transfer container holding said aromatic substance therein and mounted in the top opening of said lampshade and defining a top opening and adapted for receiving radiating heat energy from said lamp bulb, said disposable heat-transfer container having a flange formed on a top periphery thereof and hooked on a top periphery of said lampshade.

3. The aroma-diffusing night lamp assembly as claimed in claim 1, wherein said lamp bulb is selected from the group of tungsten filament-based incandescent bulb, non-filament lamp bulb and LED light bulb.

4. The aroma-diffusing night lamp assembly as claimed in claim 1, wherein said lampshade is prepared from the material group of ceramics, metal, plastics, fabrics and composite materials.

5. The aroma-diffusing night lamp assembly as claimed in claim 1, wherein said lampshade is selected made in one of transparent, semi-transparent, translucent and semi-translucent forms.

6. The aroma-diffusing night lamp assembly as claimed in claim 1, wherein said lampshade is configured to provide air vents for dissipating heat or radiating light of the lamp bulb.

7. The aroma-diffusing night lamp assembly as claimed in claim 1, wherein said air vents are configured according to a predetermined decorative design.

8. The aroma-diffusing night lamp assembly as claimed in claim 2, wherein said aroma capsule further comprises a breathing film sealed to the top opening of said disposable heat-transfer container.

9. The aroma-diffusing night lamp assembly as claimed in claim 8, wherein said breathing film is selected from the material group of nonwoven fabric, fiber cloth, woven fabric, porous plastic membrane and porous silicon rubber.

10. The aroma-diffusing night lamp assembly as claimed in claim 8, wherein said aroma capsule further comprises a sealing film bonded to said disposable heat-transfer container over said breathing film to seal said aromatic substance in said disposable heat-transfer container.

11. The aroma-diffusing night lamp assembly as claimed in claim 8, wherein said aromatic substance is a solid aromatic substance.

12. The aroma-diffusing night lamp assembly as claimed in claim 11, wherein said aromatic substance is an aromatic wax.

13. The aroma-diffusing night lamp assembly as claimed in claim 1, wherein said the aromatic substance can be an aromatic wax or a perfume block or an essential oil gel.

14. The aroma-diffusing night lamp assembly as claimed in claim 1, wherein said disposable heat-transfer container is a thin film container selected from the material group of metal, plastic, plant fiber, corn fiber, glass fiber and carbon fiber.

15. The aroma-diffusing night lamp assembly as claimed in claim 14, wherein said disposable heat-transfer container is a thin film container made of aluminum foil.

16. The aroma-diffusing night lamp assembly as claimed in claim 1, wherein said screw holder is formed with the periphery of said locating flange.

17. The aroma-diffusing night lamp assembly as claimed in claim 1, wherein said body comprises an electrically insulative socket housing consisting of a first socket housing cover shell and a second socket housing cover shell that are fixedly fastened together by said coupling socket.

* * * * *